United States Patent [19]

Kuzuna et al.

[11] 4,440,691
[45] Apr. 3, 1984

[54] INDANCARBOXYLIC ACID ZINC SALTS

[75] Inventors: Seiji Kuzuna, Kawanishi; Shoji Kishimoto, Takarazuka; Tetsuya Aono, Nagaokakyo, all of Japan

[73] Assignee: Takeda Chemical Industries, Ltd., Osaka, Japan

[21] Appl. No.: 358,215

[22] Filed: Mar. 15, 1982

[30] Foreign Application Priority Data

Mar. 19, 1981 [JP] Japan .................................. 56-41114

[51] Int. Cl.³ .............................................. C07F 3/06
[52] U.S. Cl. .................................. 260/429.9; 424/289
[58] Field of Search ...................................... 260/429.9

[56] References Cited

U.S. PATENT DOCUMENTS

| 3,644,479 | 2/1972 | Juby et al. | 260/448 R X |
| 3,663,584 | 5/1972 | Alvarez | 260/429.9 |
| 3,763,229 | 10/1973 | Noguchi | 562/492 |
| 3,975,432 | 8/1976 | Alvarez | 260/429.9 X |
| 4,214,000 | 7/1980 | Papa | 260/429.9 X |
| 4,247,715 | 1/1981 | Johnson et al. | 260/429.9 X |

Primary Examiner—Helen M. S. Sneed
Attorney, Agent, or Firm—Wegner & Bretschneider

[57] ABSTRACT

Indancarboxylic acid zinc salts of the formula:

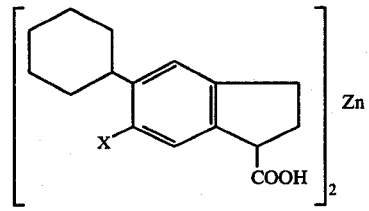

wherein X is a halogen atom, are novel compounds and have excellent pharmaceutical activities such as analgesic, antipyretic and antiinflammatory activities.

2 Claims, No Drawings

INDANCARBOXYLIC ACID ZINC SALTS

The present invention relates to novel indancarboxylic acid zinc salts having antipyretic, analgesic and antiinflammatory actions, and a method of producing said indancarboxylic acid zinc salts.

More particularly, the present invention relates to:

1. A compound of the formula:

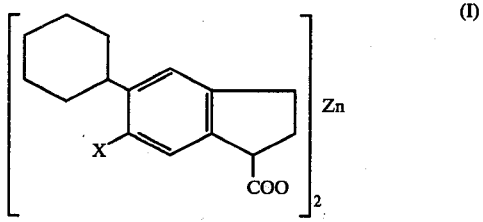

wherein X is a halogen atom.
and

2. A method of producing a compound of the formula (I), which comprises subjecting a salt of a compound of the formula:

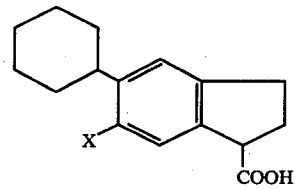

wherein X has the meaning given above, to salt interchange reaction with a zinc salt.

It is known that 5-cyclohexyl-6-haloindan-1-carboxylic acid has excellent antipyretic, analgesic and antiinflammatory actions, and the present inventors synthesized a variety of new salts and derivatives of said indancarboxylic acid and studied their physicochemical, biological and other characteristics. The investigation showed that the zinc salt of the acid has a remarkably improved biological activity as compared with the starting compound indancarboxylic acid. The present invention has been accomplished on the basis of the above finding.

Referring to the above general formulas (I) and (II), the halogen X may for example be chlorine or bromine.

The indancarboxylic acid zinc salt (I) according to the present invention contains an asymmetric carbon atom at the 1-position of the indan nucleus and the present invention encompasses both the racemic compound and the optically active compounds.

The indancarboxylic acid zinc salt (I) according to the present invention has excellent antipyretic, analgesic and antiinflammatory actions and is of low toxicity. Compared with 6-chloro-5-cyclohexylindan-1-carboxylic acid now available on the market as an antipyretic, analgesic and antiinflammatory drug, the salt has superior antipyretic, analgesic and antiinflammatory actions and is of lower toxicity. The indancarboxylic acid zinc salt (I) is useful not only as an antipyretic, analgesic and antiinflammatory drug, especially as an antirheumatic, in mammalian animals including human beings but also for the prevention and treatment of various diseases accompanying a zinc deficiency. The indancarboxylic acid zinc salt (I) can be used, either as it is or as admixed with suitable pharmaceutically acceptable excipients, vehicles, diluents, etc., in a variety of dosage forms including tablet, capsule, granule, powder, syrup, ointment, aerosol, etc. by oral or the parenteral route. While the daily dosage for an adult depends on the symptoms, age and weight of the subject patient, dosage form, route of administration, etc., the salt (I) is generally used in a dose of about 1 mg to about 1000 mg, preferably 20 mg to 40 mg, orally or about 1 mg to 1000 mg, preferably 10 mg to 40 mg, parenterally.

The indancarboxylic acid zinc salt of the general formula (I) can be obtained by subjecting a salt of a compound of the general formula (II) to salt interchange reaction with a zinc salt.

The salt of compound (II) may be any type of salt that may undergo salt interchange reaction with a zinc salt. Thus for example, the alkali metal (e.g. sodium, potassium, lithium) salts, alkaline earth metal (berrylium, magnesium, calcium, strontium, barium, radium) salts, and ammonium salts of compound (II) may be mentioned.

The zinc salt mentioned above may be any type of salt that may undergo salt interchange reaction with the salt of compound (II), and is a compound of the general formula:

$$Zn(X^1)_2 \qquad (III)$$

($X^1$ is a monovalent anion or, as $(X^1)_2$, represents a divalent anion). As specific examples of $X^1$, there may be mentioned halogens (e.g. chlorine, bromine), OH, lower acyloxy (e.g. formyloxy, acetyloxy, propionyloxy, butyryloxy), etc., and examples of $(X^1)_2$ include carbonate, sulfate and other radicals.

The salt interchange reaction according to the present invention may be conducted in the per se conventional manner. An exemplary method comprises dissolving the salt of (II) and the zinc salt in an appropriate solvent capable of dissolving both and causing the compound (I) to precipitate out. The most suitable solvent is water but it is also possible to emply an organic solvent such as an alcohol (e.g. methanol, ethanol), tetrahydrofuran, dioxane, dimethylformamide, etc. in combination with water.

Depending on the type of solvent used, the desired compound (I) separates out on mere dissolution of the salt of (II) and the zinc salt therein. If not, the solution is, for instance, heated or cooled or the solution is modified by addition of a solvent that will dissolve the salt of (II) and the zinc salt but will not dissolve the compound (I), whereby the compound (I) can be obtained.

When the salt of (II) is an alkali metal or ammonium salt, the zinc salt is a zinc halide, zinc hydroxide, zinc lower-carboxylate, zinc carbonate or zinc sulfate, and the solvent is water, the desired compound (II) can be caused to separate out by stirring the solution of the salt of (II) and the zinc salt in water either under cooling or at room temperature for a few minutes to a few hours.

The indancarboxylic acid zinc salt (I) thus obtained can be isolated by the per se conventional separation and purification procedures.

The salt of compound (II) employed as a starting compound in the above method can be easily prepared by a conventional method for the formation of a salt from an acid, e.g. by reacting a compound of the general formula (II) with sodium hydroxide, potassium hydroxide, aqueous ammonia or the like.

The following working and experimental examples are given to illustrate the present invention in further detail.

Experimental Example

1. Test compounds

Compound A: 6-Chloro-5-cyclohexylindan-1-carboxylic acid (reference)

Compound B: 6-Chloro-5-cyclohexylindan-1-carboxylic acid zinc salt (a compound of this invention)

2. Procedures (a) Antiinflammatory activity (nystatin-induced edema)

Jcl:ICR mice (male, b.w. 24 to 35 g) in groups of 10 animals were orally dosed with test compounds and after 30 minutes an edema was produced in each mouse by injecting 0.025 ml of a 1% suspension of nystatin with 2% gum arabic in physiological saline subcutaneously at the right hind paw. The edema was measured 6 hours after the administration of nystatin. Each animal was sacrificed by cervical dislocation and the right and left hind paws were immediately cut off with scissors at the ankle. The weight gain due to the edema was estimated from the weight differences of the right and left hind paws of the same mouse.

TABLE 1

| Test compound | Dosage mg/kg | Number of animals | (mg ± S.e) | % Inhibition |
|---|---|---|---|---|
| Control | — | 10 | 94.28 ± 3.69 | — |
| Compound A | 6.25 | 10 | 86.14 ± 6.06 | 8.6 |
| (reference) | 12.5 | 10 | 82.22 ± 3.54* | 12.8 |
| Compound B | 6.25 | 10 | 82.50 ± 3.80* | 12.5 |
| (this invention) | 12.5 | 10 | 75.67 ± 3.33** | 19.7 |

*$P < 0.05$,
**$P < 0.01$ (b) Antipyretic activity [the fever induced by bacterial (*Escherichia coli*) endotoxin]

Fever was produced in albino rabbits (male, Seiwa Experimental Animal Laboratory, b.w. 2.6 to 3.3 kg) by injecting 2 μg/kg of *E. coli* endotoxin intravenously into each animal. The rectal temperature was determined at one-hour, two hour, three hour, four hour and five hour after the injection. Each test compound was orally administered in an amount of 5 mg/kg 1.5 hours after endotoxin treatment.

TABLE 2

| | Rectal temperature (°C.) | | | | |
|---|---|---|---|---|---|
| | The time (hrs.) after endotoxin treatment | | | | |
| Test compound | 1 | 2 | 3 | 4 | 5 |
| Control | 39.8 | 39.7 | 40.2 | 39.9 | 39.4 |
| Compound A (reference) | 39.8 | 39.4 | 39.5** | 39.2** | 38.8* |
| Compound B (the invention) | 39.8 | 39.6 | 39.0** | 38.9** | 38.7* |

↑ Drug

*$P < 0.05$,
**$P < 0.01$

Example

In 100 ml of water was dissolved 0.4 g of sodium hydroxide, and under cooling with ice-water, 2.8 g of 6-chloro-5-cyclohexylindan-1-carboxylic acid was added. The mixture was shaken well and filtered. To the filtrate was added a solution of 1.4 g of zinc chloride in 5 ml of water. The mixture was stirred for an hour, then the resulting precipitate was collected by filtration, rinsed thoroughly with water, and dried in vacuo over phosphorus pentoxide to give zinc 6-chloro-5-cyclohexylindan-1-carboxylate (racemic). Yield 3.2 g. m.p. 150°–155° C. (trihydrate).

Elemental analysis: Calcd. for $C_{32}H_{36}O_4Cl_2.Zn.3-H_2O$: C, 56.96; H, 6.27; Cl, 10.51. Found: C, 57.14; H, 6.23; Cl, 10.62.

A typical formulation for the compound of this invention as an analgesic, antipyretic or antiinflammatory agent is as follows:

| | (Tablet) | |
|---|---|---|
| (1) | 6-chloro-5-cyclohexyl-1-indancarboxylic acid zinc salt | 10 mg |
| (2) | Spray dried lactose | 184.5 mg |
| (3) | Colloidal silicon dioxide | 0.5 mg |
| (4) | Microcrystalline cellulose | 30 mg |
| (5) | Magnesium stearate | 5 mg |
| | | 230 mg |

The ingredients (1), (2), (3) and (4) are admixed in a suitable blender. Then, the ingredient (5) is added to the mixture. The whole mixture is comprssed into a tablet.

| | (Capsule) | |
|---|---|---|
| (1) | 6-chloro-5-cyclohexyl-1-indancarboxylic acid zinc salt | 10 mg |
| (2) | Microcystalline cellulose | 30 mg |
| (3) | Lactose | 57 mg |
| (4) | Magnesium stearate | 3 mg |
| | | 100 mg |

The above ingredients are mixed and a gelatin capsule is filled with the mixture to prepare a capsulated preparation.

| | (Tablet) | |
|---|---|---|
| (1) | 6-chloro-5-cyclohexyl-1-indancarboxylic acid zinc salt | 30 mg |
| (2) | Lactose | 44 mg |
| (3) | Starch | 10.6 mg |
| (4) | Starch (for making paste) | 5 mg |
| (5) | Magnesium stearate | 0.4 mg |
| (6) | Carboxymethylcellulose calcium | 20 mg |
| | | 110 mg |

The above ingredients are mixed and made into a tablet by a conventional wet granulation method.

| | (Soft capsule) | |
|---|---|---|
| (1) | 6-chloro-5-cyclohexyl-1-indancarboxylic acid zinc salt | 30 mg |
| (2) | Corn oil | 110 mg |
| | | 140 mg |

The above ingredients are mixed to make a paste and then a soft capsule is filled with the solution in a conventional manner.

| | (Hydrophilic ointment) | |
|---|---|---|
| (1) | 6-chloro-5-cyclohexyl-1-indancarboxylic acid zinc salt | 1.0 g |

| (Hydrophilic ointment) | | |
| --- | --- | --- |
| (2) | Stearyl alcohol | 20.0 g |
| (3) | White petrolatum | 25.0 g |
| (4) | Propylene glycol | 15.0 g |
| (5) | Sodium lauryl sulfate | 1.5 g |
| (6) | Methyl p-hydroxybenzoate | 0.2 g |
| (7) | Propyl p-hydroxybenzoate | 0.1 g |
| (8) | Purified water | 37.2 g |
| | | 100.0 g |

The above ingredients (1), (2), (3) and (7) are homogeneously mixed under heating to give a mixture A (Oily phase). The remaining ingredients (4), (5), (6) and (8) are homogeneously mixed under heating to give a mixture B (Aqueous phase). The mixture B is added gradually to the mixture A under heating with stirring to emulsify, and then the whole mixture is cooled.

| (Washable ointment) | | |
| --- | --- | --- |
| (1) | 6-chloro-5-cyclohexyl-1-indancarboxylic acid zinc salt | 1.0 g |
| (2) | Polyethylene glycol 4000 | 45.0 g |
| (3) | Polyethylene glycol 400 | 54.0 g |
| | | 100.0 g |

The above ingredients (2) and (3) are homogeneously mixed under heating to give a mixture A, and the mixture A is homogeneously admixed with the ingredient (1) in a conventional manner.

What is claimed is:

1. A compound of the formula:

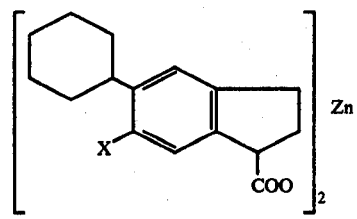

wherein X is a halogen atom.

2. A compound as claimed in claim 1, wherein the compound is 6-chloro-5-cyclohexyl-1-indancarboxylic acid zinc salt.

* * * * *